United States Patent [19]
Kolenik et al.

[11] 4,300,567
[45] Nov. 17, 1981

[54] METHOD AND APPARATUS FOR EFFECTING AUTOMATIC VENTRICULAR DEFIBRILLATION AND/OR DEMAND CARDIOVERSION THROUGH THE MEANS OF AN IMPLANTED AUTOMATIC DEFIBRILLATOR

[75] Inventors: Steve Kolenik, Leechburg; Alois A. Langer, Pittsburgh, both of Pa.

[73] Assignee: Mieczyslaw Mirowski, Owings Mills, Md.

[21] Appl. No.: 120,100

[22] Filed: Feb. 11, 1980

[51] Int. Cl.³ ............................................. A61N 1/36
[52] U.S. Cl. .................................................. 128/419 D
[58] Field of Search ......... 128/419 D, 419 P, 419 PG

[56] References Cited
U.S. PATENT DOCUMENTS

| | | | |
|---|---|---|---|
| 3,756,245 | 9/1973 | Thaler et al. | 128/419 PG |
| 3,805,795 | 4/1974 | Denniston et al. | 128/419 D |
| 3,857,398 | 12/1974 | Rubin | 128/419 D |
| 3,881,493 | 5/1975 | Cannon | 128/419 PG |
| 3,952,750 | 4/1976 | Mirowski et al. | 128/419 D |

OTHER PUBLICATIONS

Trevino et al., "American Heart Journal" vol. 81, No. 1, Jan. 1971, pp. 20-28.
Schuder et al., "Transactions of the American Society for Artificial Internal Organs" vol. 16, 1970, pp. 207-212.

*Primary Examiner*—William E. Kamm
*Attorney, Agent, or Firm*—Fleit & Jacobson

[57] ABSTRACT

A method and apparatus for effecting automatic ventricular defibrillation and/or demand cardioversion comprises an implanted automatic defibrillator having a normal (ventricular defibrillation) mode of operation and a cardioverting (demand cardioversion) mode of operation. One embodiment of the invention includes a simulated fibrillation source, externally located, for applying a simulated fibrillation signal to the patient via corresponding electrodes, the internal automatic defibrillator detecting the simulated fibrillation signal and responding thereto so as to apply a defibrillating voltage (in the normal mode) or a cardioverting voltage (in the cardioverting mode) to the heart of the patient. Another embodiment of the invention also includes an external command system, by means of which the implanted automatic defibrillator is actuated from the normal mode to the cardioverting mode, to reduce the discharge energy level, to cardiovert in synchronization with the QRS complex, or both.

24 Claims, 2 Drawing Figures

METHOD AND APPARATUS FOR EFFECTING AUTOMATIC VENTRICULAR DEFIBRILLATION AND/OR DEMAND CARDIOVERSION THROUGH THE MEANS OF AN IMPLANTED AUTOMATIC DEFIBRILLATOR

BACKGROUND OF THE INVENTION

1. Field of the Invention

The present invention relates to a method and apparatus for effecting automatic ventricular defibrillation and/or demand cardioversion through the means of an implanted automatic defibrillator. More particularly, the invention relates to an implantable device responsive to ventricular fibrillation for automatically defibrillating a patient, and further responsive to a simulated fibrillation signal to become a demand cardioversion device capable of treating non-lethal arrhythmias.

2. Description of the Prior Art

There continues to be a need for devices which, automatically or upon demand, as the case may be, rapidly and efficiently perform defibrillation and/or cardioversion functions in order to correct any one of a number of lethal and non-lethal arrhythmic heart conditions, including atrial tachycardia, atrial flutter, atrial fibrillation, junctional rhythms, ventricular tachycardia, ventricular flutter, and ventricular fibrillation, as well as any other non-pacing related arrhythmic condition correctable by applying electric shocks to the heart.

Past efforts have included the development of a command atrial cardioverting device, such as is disclosed in U.S. Pat. No. 3,952,750 to Mirowski et al, for the treatment of non-lethal arrhythmias. Such a device provides correction of atrial fibrillation, flutter or tachycardia by two alternative techniques: command by the patient using a magnet to cause closure of a relay beneath the surface of the skin so as to effect the needed cardioversion; or command by a physician who operates a command device to transmit command signals received by a miniature receiver located in the cardioversion device implanted in the patient. As further disclosed in the aforementioned patent, the cardioversion device then synchronously (that is, in synchronization with the QRS complex as detected by an ECG monitor) cardioverts the heart.

Another development in the treatment of heart disease consists of the method and apparatus for monitoring heart activity and for automatically treating lethal arrhythmias. Examples of a recent method and apparatus are disclosed in copending applications of Langer et al, U.S. Ser. Nos. 878,005 and 878,006, now U.S. Pat. Nos. 4,202,340 and 4,184,493, respectively. These applications disclose a highly sophisticated technique for detecting and reacting to ventricular fibrillation, entailing sensing ECG signals from the heart, shaping of such signals, performing a discrimination function and an averaging function relative to the shaped signals, examining the averaged signals to determine whether predetermined threshold limits are met, and then effecting defibrillation if the predetermined threshold limits are not met.

SUMMARY OF THE INVENTION

According to a first aspect of the present invention, there is provided a method and a combination of elements, including an implantable, fully automatic defibrillator, for automatically defibrillating a patient suffering from lethal ventricular fibrillation, and for effecting demand cardioversion upon the application of a simulated fibrillation signal injected through the skin of the patient. More particularly, in accordance with the latter aspect of the invention, a simulated fibrillation signal is applied through the skin of a patient, attenuated by the body of the patient, and then sensed by the sensing electrodes of an automatic ventricular defibrillator implanted in the body of the patient. Such a signal can be a 10–20 Hz. sine wave of a voltage level reasonably tolerable by the patient (for example, 2–10 volts applied to the patient's skin), which signal, when detected by the implanted automatic ventricular defibrillator actuates the latter to the "discharge" state.

In accordance with a further aspect of the present invention, an external command signal is used to cause the implanted automatic defibrillator to operate in a cardioverting mode, and to be capable of delivering cardioverting pulses of energy levels lower than typical ventricular defibrillation energy levels. The external command signal employed to cause the implanted automatic defibrillator to become a cardioversion device, in one embodiment, is brought about by the placement of a magnet in contact with the skin of the patient to close a normally open implanted reed switch (that is, open in the normal mode for ventricular defibrillation), and thereby to cause the implanted device to assume the cardioverting mode.

As a further embodiment of the present invention, the external command signal comprises coded magnetic pulses provided, via an implanted receiver, to a control register, or the like, and thence to a digital-to-analog converter, such as disclosed in the aforementioned applications (Ser. Nos. 878,004 and 878,006) of Langer et al.

Therefore, a principal object of the present invention is to provide a method and an apparatus for effecting fully automatic ventricular defibrillation of a patient suffering from lethal ventricular fibrillation.

A further object of the present invention is to provide a method and an apparatus for utilizing an implanted, fully automatic ventricular defibrillator as a demand cardioverter.

Another object of the present invention is to provide a method and a combination of elements, including an implantable, fully automatic defibrillator, for effecting demand cardioversion of a patient upon the application of a simulated fibrillation signal injected through the skin of the patient.

Another object of the present invention is to provide a method and an apparatus employing a fully automatic defibrillator which is responsive to an external command signal to operate in the cardioverting mode, and to be capable of delivering cardioverting pulses to a patient for the treatment of a non-lethal arrhythmia.

Another object of the present invention is to provide a method and an apparatus for programming, into a fully automatic ventricular defibrillator, the ability to issue cardioverting pulses, on demand, at energy levels below those typically used for ventricular defibrillation.

Still a further object of the invention is to provide a method and apparatus for applying synchronized cardioverting pulses, upon demand, by means of a fully automatic ventricular defibrillator.

The above and other objects that will hereinafter appear, and the nature of the invention, will be more clearly understood by reference to the following description, the appended claims, and the accompanying drawings.

DETAILED DESCRIPTION

The invention of the application will now be more fully described with reference to FIG. 1, which is a diagrammatic representation of the system of the present invention for effecting automatic verticular defibrillation and/or demand cardioversion.

Figure 1:
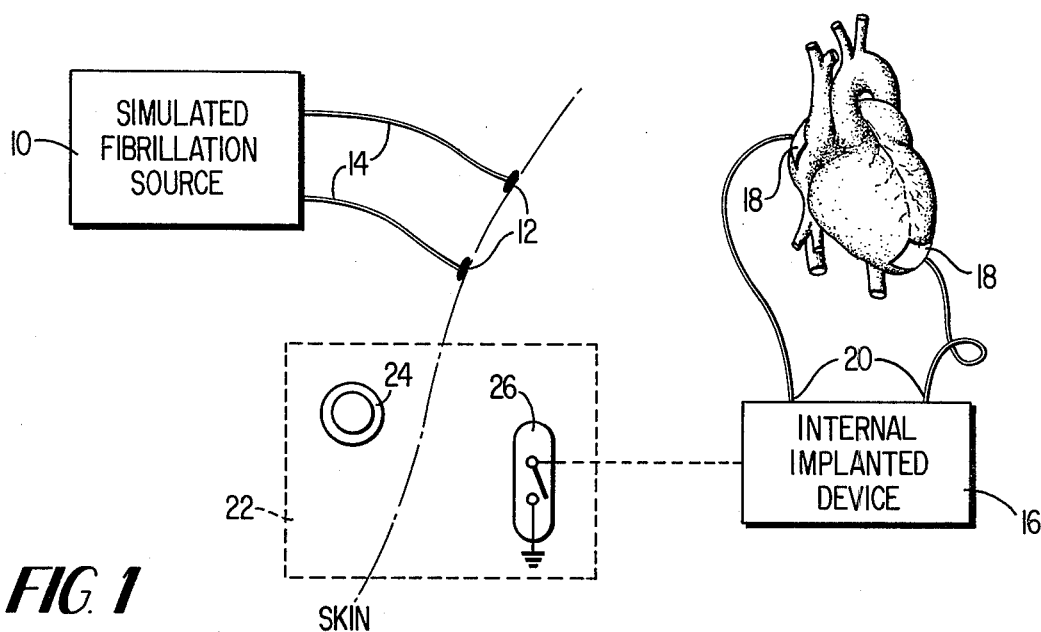
FIG. 1 is a diagrammatic representation of the system of the present invention for effecting automatic ventricular defibrillation and/or demand cardioversion.

Referring to FIG. 1, the system of the present invention principally comprises an internal implanted device 16 connected to heart electrodes 18 via corresponding leads 20. The implanted device 16 is a fully automatic ventricular defibrillator, with complete defibrillation sensing circuitry such as disclosed in U.S. patent application No. 878,006 of Langer et al. Moreover, the internal implanted device 16 operates in a fully automatic manner, as described in the latter application, to detect ventricular fibrillation, and to provide to the heart of the patient, via leads 20 and electrodes 18, a defibrillation voltage so as to treat the detected, lethal, ventricular fibrillation.

Further referring to FIG. 1, the system of the present invention is seen to further comprise a simulated fibrillation source 10, and a pair of electrodes 12 externally positioned on the skin of the patient in proximity to the heart 18, and connected to the simulated fibrillation source 10 via leads 14. The arrangement described thus far constitutes the most simplified form of a demand cardioverter in accordance with the present invention.

The general operation of the most simplified form of demand cardioverter is as follows. Upon determination that there is need for elective cardioversion, for example, as in the case of atrial fibrillation, the simulated fibrillation source 10 is brought into proximity to the patient as shown in FIG. 1, and is actuated to provide a simulated fibrillation signal (for example, in the 2–10 volt amplitude range) through the skin of the patient via leads 14 and electrodes 12. Such signal will be attenuated by the body, and will reach the heart electrodes 18 (in the example, in the 2–10 millivolt amplitude range). The injected fibrillation signals are detected at electrodes 18, and are interpreted by the sensing circuits in the implanted device 16 as indicating the need for ventricular defibrillation. Then, the automatic defibrillator actuates its inverter circuit, charges its discharge capacitor, and releases the energy stored by the capacitor for delivery to the heart. Such operation can be carried out without alteration of the automatic implantable defibrillator disclosed, for example, in the aforementioned Langer et al applications.

In another form of the present invention, referring to FIG. 1, the system of the present invention comprises an external command system 22 made up of an externally located magnet 24 and an implanted reed switch 26 (in the case of the internal implanted device 16). Thus, when it is desired to effect demand cardioversion utilizing the automatic ventricular defibrillator (that is, device 16), the magnet 24 is brought into proximity to the normally open reed switch 26 so as to close the reed switch 26, and, thus, to convert the internal implanted device 16 from its normal (automatic ventricular defibrillation) mode of operation to the cardioverting mode of operation. Then, with reed switch 24 closed, any one or more special cardioversion mode operations (described below) can be carried out. As mentioned earlier, the external command system 22, just described in terms of the magnet 24 and reed switch 26, can be implemented, in a further embodiment of the present invention, by means of coded magnetic pulses, transmitted and modulated RF command signals, or program-generated command signals.

It is to be noted that, by using the external command system 22, the present invention is able to achieve complete adaptation of the internal implanted (ventricular defibrillator) device 16 to a cardioverting device. That is to say, the device 16 is able to produce cardioverting pulses which are typically of lower energy levels than ventricular defibrillating pulses, and is able to produce such cardioverting pulses in synchronization with the QRS complex of the patient's heart.

Figure 2:
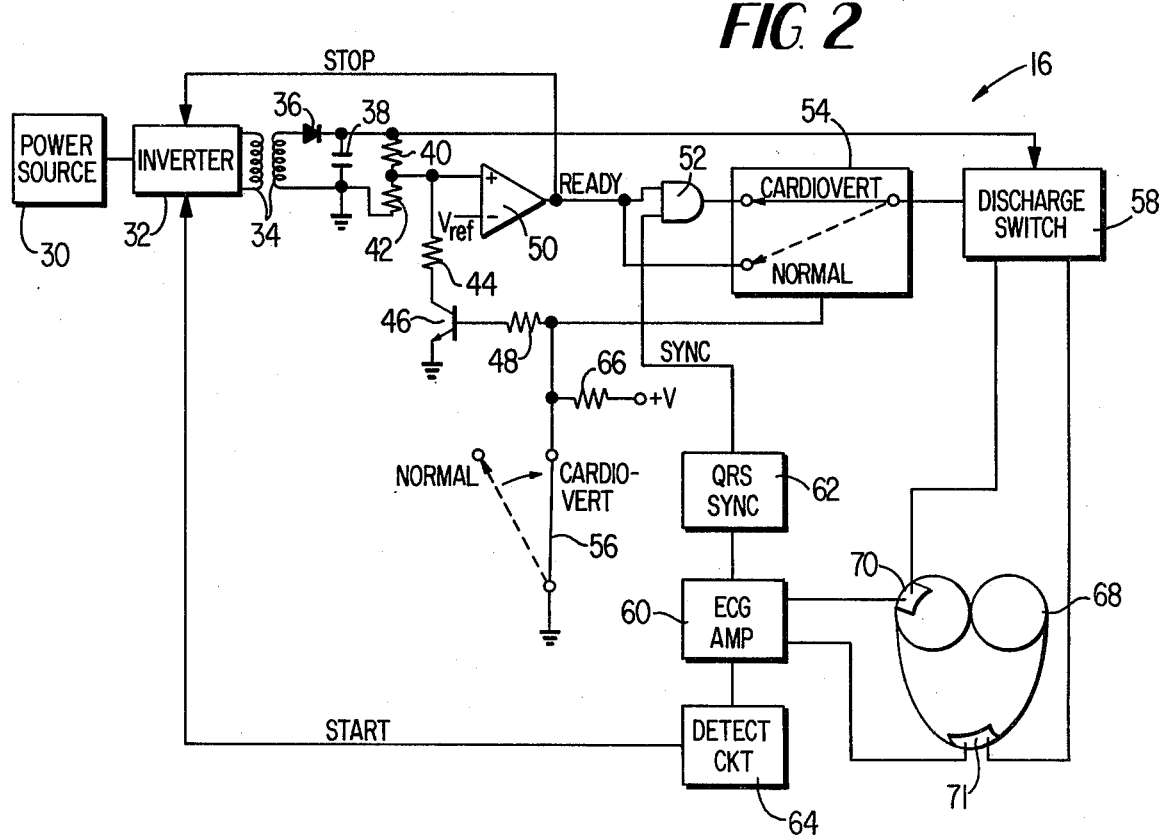
FIG. 2 is a detailed schematic of the internal implanted device 16 of FIG. 1.

Turning, then, to FIG. 2, there is shown a detailed schematic of the internal implanted device 16 of FIG. 1, equipped with special cardioversion circuitry. The device 16 comprises a power source 30, inverter 32, transformer 34, forward-biased diode 36, discharge capacitor 38, input and voltage-dividing resistors 40, 42 and 44, NPN transistor 46 and associated base resistor 48, comparator 50, AND gate 52, mode switches 54 and 56, discharge switch 58, ECG amplifier 60, QRS sync circuit 62, and detection circuitry 64. The base of transistor 46 is controlled by a positive supply voltage +V, supplied via series-connected resistors 66 and 48, the junction between resistors 66 and 48 being connected to ground via mode switch 56. Discharge switch 58 is connected to the heart 68 via conventional electrodes 70 and 71, the latter also being connected to the ECG amplifier 60. Finally, it is to be noted that the mode switches 54 and 56 of FIG. 3 correspond to the reed switch 26 of FIG. 1 which, as previously explained, is actuated from its normally open (ventricular defibrillation) position to its closed (cardioversion) position by the magnet 24.

In operation, the internal implanted device 16 of FIG. 2 detects the need for defibrillation by means of ECG amplifier 60 which detects either a normal fibrillation signal or a simulated fibrillation signal (the 10–20 Hz sine wave) applied by the simulated fibrillation source 10 (FIG. 1) through the skin of the patient of the heart 68 (FIG. 2). Upon detection thereof, ECG amplifier 60 actuates detection circuitry 64 which, in a conventional manner (for example, as disclosed in aforementioned applications Ser. Nos. 878,004 and 878,006 of Langer et al), generates a START command to the inverter 32. In this manner, the power source 30 is permitted to charge capacitor 38 via the inverter 32, the transformer 34 and the forward-biased diode 36. Once the voltage built up on capacitor 38 reaches a predetermined level (the particular predetermined level depending on whether the normal or cardioverting mode of operation is being employed), comparator 50 detects that condition and issues the READY command directly to the discharge switch 58 (in the normal mode, as dictated by mode switch 54), or, alternatively, indirectly via AND gate 52 to the discharge switch 58 (in the cardioverting mode, as dictated by the switch 54). That is to say, in the cardioverting mode, the READY command is AND'ed with the SYNC command from the QRS sync circuit 62 (connected to ECG amplifier 60). In this manner, in the cardioverting mode of operation, the actuation of discharge switch 58, so as to apply the cardioverting pulse to the heart 68, is synchronized with the QRS waveform of the heart, as is typical under conventional cardioverting techniques.

Further referring to FIG. 2, it is to be noted that the switch 56 is in the open position during the normal mode of operation. Therefore, the input to the base of transistor 46 is "high," causing transistor 46 to conduct. Thus, the resistor 44 and transistor 46 serve a voltage-dividing function with respect to the voltage applied to the positive input of comparator 50, resulting in issuance of a READY command only after a relatively large (defibrillating) voltage has built up across capacitor 38. Conversely, in the cardioverting mode of operation, the switch 56 is actuated to the closed position, resulting in application of a "low" input to the base of transistor 46, in turn causing transistor 46 to be non-conductive. Therefore, resistor 44 and transistor 46 do not function as a voltage-dividing network with respect to the positive input to comparator 50, and the READY command is issued after a relatively low energy (cardioverting) voltage has developed across capacitor 38. In this manner, device 16 provides a relatively large (defibrillating) voltage or a lesser (cardioverting) voltage, depending on the particular mode (normal or cardioverting) selected via switch 56.

It is further to be noted that the "high" and "low" inputs applied to the base resistor 48 of transistor 46 are also applied to the mode switch 54, and cause that switch to be actuated to the open position (normal mode) or closed position (cardioverting mode). Of course, the same effect could be achieved by other means, for example, by gangconnecting switches 56 and 54.

As a result of the present invention, therefore, internal implanted device 16 functions in two modes: (1) a normal mode of operation, whereby a higher voltage is built up across capacitor 38, and is discharged through discharge switch 58 into the heart 68 without QRS synchronization, for the purpose of achieving ventricular defibrillation; and (2) a cardioverting mode of operation, whereby a cardioverting voltage of lower level is built up across capacitor 38, and is discharged through discharge switch 58 into the heart 68 for the purpose of achieving demand cardioversion, such being accomplished in synchronization with the QRS complex of the heart waveform, as detected by QRS sync circuit 62, which provides its synchronizing output SYNC to the AND gate 52 in order to synchronize the cardioverting pulse with the QRS complex. Alternatively, the present invention contemplates that the cardioverting mode operate either with low discharge energy alone or with QRS synchronization alone.

Finally, it is to be noted that the output of comparator 50 also serves as a STOP command, causing the inverter 32 to stop build-up of voltage across capacitor 38 via the transformer 34 and the forward-biased diode 36.

While preferred forms and arrangements have been shown in illustrating the invention, it is to be clearly understood that various changes in detail and arrangement may be made without departing from the spirit and scope of this disclosure.

We claim:

1. A method of effecting demand cardioversion of a patient by means of an implanted automatic defibrillator, comprising the steps of:

applying a simulated fibrillation signal to the skin of the patient;
   sensing the simulated fibrillation signal by means of the implanted automatic defibrillator; and
   in response to said sensed simulated fibrillation signal, converting the implanted automatic defibrillator to a cardioverting device and actuating the implanted automatic defibrillator to effect demand cardioversion of the patient.

2. The method of claim 1, wherein said converting step comprises generating an external command signal which, when sensed by said implanted automatic defibrillator, converts said implanted automatic defibrillator to a cardioverting device by lowering the discharge energy level of the automatic defibrillator.

3. The method of claim 2, wherein said step of generating said external command signal comprises the steps of bringing a magnet close to the skin of the patient in proximity to an implanted reed switch, implanted under the skin of the patient, so as to actuate said implanted reed switch, whereby to convert the implanted automatic defibrillator to a cardioverting device.

4. The method of claim 2, wherein said external command signal, when sensed by said implanted automatic defibrillator, converts said implanted automatic defibrillator to a cardioverting device by additionally effecting demand cardioversion in synchronization with the patient's QRS complex.

5. The method of claim 1, wherein said step of converting the implanted automatic defibrillator to a cardioverting device comprises programming said implanted automatic defibrillator to generate a mode-changing signal, and applying said mode-changing signal to said implanted automatic defibrillator, whereby to convert said implanted automatic defibrillator to a cardioverting device.

6. The method of claim 1, wherein said converting step comprises generating an external command signal which, when sensed by said implanted automatic defibrillator, converts said implanted automatic defibrillator to a cardioverting device by effecting demand cardioversion in synchronization with the patient's QRS complex.

7. An apparatus for effecting demand cardioversion of a patient, comprising:

means for applying a simulated fibrillation signal to the skin of the patient; and
   an implanted automatic defibrillator, including sensing means for sensing the simulated fibrillation signal, converting means for converting the implanted automatic defibrillator to a cardioverting device, and actuating means responsive to said sensed simulated fibrillation signal for effecting demand cardioversion of the patient.

8. The apparatus of claim 6, wherein said converting means comprises generating means for generating an external command signal, said implanted automatic defibrillator including receiving means for receiving said external command signal and for responding thereto for converting to said cardioverting device.

9. The apparatus of claim 8, wherein said generating means comprises a magnet external to the skin of the patient, said receiving means comprising a reed switch implanted under the skin of the patient and responsive to said magnet, when said magnet is in proximity to the skin of the patient, for being actuated to a closed position, whereby to convert said implanted automatic defibrillator to said cardioverting device.

10. The apparatus of claim 6, wherein said actuating means comprises a detection circuit for issuing a start signal, said implanted automatic defibrillator further comprising a power source, a discharge circuit, and applying means responsive to said start signal from said detection circuit for applying power from said power source to said discharge circuit.

11. The apparatus of claim 10, wherein said discharge circuit comprises capacitor means for receiving power from said power source and for building up a voltage therein, said discharge circuit further comprising threshold detection means for detecting when said voltage built up in said capacitor means has reached a predetermined level, and thereupon issuing a ready signal.

12. The apparatus of claim 11, wherein said apparatus has at least a normal mode of operation, said discharge circuit comprising mode switch means responsive to said normal mode of operation for assuming a given state, and a discharge switch connected to said capacitor means and to said mode switch means, said mode switch means being responsive, when in said given state, to said ready signal for actuating said discharge switch to provide said voltage built up in said capacitor means to the heart of the patient, whereby to effect automatic defibrillation of said patient.

13. The apparatus of claim 11, wherein said apparatus has at least a cardioverting mode of operation, said discharge circuit comprising mode switch means responsive to said cardioverting mode of operation for assuming a given state, QRS synchronism means connected to said sensing means and responsive to the sensing of said simulated fibrillation signal for issuing a synchronization signal, and AND gate means connected to said threshold detection means for receiving said ready signal, said AND gate means being responsive, in said cardioverting mode of operation of said apparatus, to said reception of said ready signal and said synchronization signal, for issuing an enabling signal, said discharge circuit further comprising a discharge switch, said mode switch means being connected to said AND gate means for receiving said enabling signal, and responsive thereto, when in said given state, for passing said enabling signal to said discharge circuit, said discharge circuit being connected to said capacitor means, and being responsive to said enabling signal from said mode switch means for providing said voltage built up in said capacitor means to the heart of the patient, whereby to effect demand cardioversion of said patient.

14. The apparatus of claim 11, wherein said apparatus has a normal mode of operation and a cardioverting mode of operation, said discharge circuit further comprising mode switch means for assuming a first state in said normal mode and a second state in said cardioverting mode, and adjusting means responsive to said first and second states, respectively, of said mode switch means for correspondingly adjusting said predetermined value of voltage built up in said capacitor means, as detected by said threshold level detection means.

15. The apparatus of claim 11, further comprising means for limiting the value of energy discharged by said capacitor means once said predetermined level of voltage, as built up in said capacitor means, is detected by said threshold detection means.

16. An implanted automatic defibrillator for effecting demand cardioversion of a patient in response to application of a simulated fibrillation signal to the skin of the patient, comprising:

sensing means for sensing the simulated fibrillation signal;
converting means for converting the implanted automatic defibrillator to a cardioverting device; and
actuating means responsive to said sensed simulated fibrillation signal for effecting demand cardioversion of the patient.

17. The defibrillator of claim 16, wherein said converting means comprises generating means for generating an external command signal, said implanted automatic defibrillator including receiving means for receiving said external command signal and for responding thereto for converting to said cardioverting device.

18. The defibrillator of claim 17, wherein said generating means comprises a magnet external to the skin of the patient, said receiving means comprising a reed switch implanted under the skin of the patient and responsive to said magnet, when in proximity to the skin of the patient, for being actuated to a closed position, whereby to convert said implanted automatic defibrillator to said cardioverting device.

19. The defibrillator of claim 16, wherein said actuating means comprises a detection circuit for issuing a start signal, said implanted automatic defibrillator further comprising a power source, a discharge circuit, and applying means responsive to said start signal from said detection circuit for applying power from said power source to said discharge circuit.

20. The defibrillator of claim 19, wherein said discharge circuit comprises capacitor means for receiving power from said power source and for building up a voltage therein, said discharge circuit further comprising threshold detection means for detecting when said voltage built up in said capacitor means has reached a predetermined level, and thereupon issuing a ready signal.

21. The defibrillator of claim 20, wherein said apparatus has at least a normal mode of operation, said discharge circuit comprising mode switch means responsive to said normal mode of operation for assuming a given state, and a discharge switch connected to said capacitor means and to said mode switch means, said mode switch means being responsive, when in said given state, to said ready signal for actuating said discharge switch to provide said voltage built up in said capacitor means to the heart of the patient, whereby to effect automatic defibrillation of said patient.

22. The defibrillator of claim 20, wherein said apparatus has at least a cardioverting mode of operation, said discharge circuit comprising mode switch means responsive to said cardioverting mode of operation for assuming a given state, QRS synchronism means connected to said sensing means and responsive to the sensing of said simulated fibrillation signal for issuing a synchronization signal, and AND gate means connected to said threshold detection means for receiving said ready signal, said AND gate means being responsive, in said cardioverting mode of operation of said apparatus, to said reception of said ready signal and said synchronization signal, for issuing an enabling signal, said discharge circuit further comprising a discharge switch, said mode switch means being connected to said AND gate means for receiving said enabling signal, and responsive thereto, when in said given state, for passing said enabling signal to said discharge circuit, said discharge circuit being connected to said capacitor means, and being responsive to said enabling signal from said mode switch means for providing said voltage built up in said capacitor means to the heart of the patient, whereby to effect demand cardioversion of said patient.

23. The defibrillator of claim 20, wherein said apparatus has a normal mode of operation and a cardioverting mode of operation, said discharge circuit further comprising mode switch means for assuming a first state in said normal mode and a second state in said cardioverting mode, and adjusting means responsive to said first and second states, respectively, of said mode switch means for correspondingly adjusting said predetermined value of voltage built up in said capacitor means, as detected by said threshold level detection means.

24. The defibrillator of claim 20, further comprising means for limiting the value of energy discharged by said capacitor means once said predetermined level of voltage, as built up in said capacitor means, is detected by said threshold detection means.

* * * * *